(12) United States Patent
Ueda et al.

(10) Patent No.: US 10,690,606 B2
(45) Date of Patent: Jun. 23, 2020

(54) HYDROGEN SENSOR

(71) Applicant: KOA CORPORATION, Nagano (JP)

(72) Inventors: Toshitsugu Ueda, Fukuoka (JP); Hiroshi Oigawa, Nagano (JP)

(73) Assignee: KOA CORPORATION, Nagano (JP)

(*) Notice: Subject to any disclaimer, the term of this patent is extended or adjusted under 35 U.S.C. 154(b) by 260 days.

(21) Appl. No.: 15/759,343

(22) PCT Filed: Sep. 16, 2016

(86) PCT No.: PCT/JP2016/077367
§ 371 (c)(1),
(2) Date: Mar. 12, 2018

(87) PCT Pub. No.: WO2017/047728
PCT Pub. Date: Mar. 23, 2017

(65) Prior Publication Data
US 2018/0252658 A1 Sep. 6, 2018

(30) Foreign Application Priority Data
Sep. 16, 2015 (JP) .................. 2015-183106

(51) Int. Cl.
*G01N 25/22* (2006.01)
*G01N 33/00* (2006.01)

(52) U.S. Cl.
CPC .......... *G01N 25/22* (2013.01); *G01N 33/005* (2013.01)

(58) Field of Classification Search
CPC .............................. G01N 25/22; G01N 33/005
See application file for complete search history.

(56) References Cited

U.S. PATENT DOCUMENTS 4,000,089 A * 12/1976 Senda .................... G01N 27/12
252/514
4,394,239 A * 7/1983 Kitzelmann ....... G01N 27/4045
204/414

(Continued)

FOREIGN PATENT DOCUMENTS

JP 55-94558 6/1980
JP 2008-39658 2/2008

(Continued)

OTHER PUBLICATIONS

Official Communication issued in International Patent Application No. PCT/JP2016/077367, dated Dec. 13, 2016.

*Primary Examiner* — Lisa M Caputo
*Assistant Examiner* — Philip L Cotey
(74) *Attorney, Agent, or Firm* — Greenblum & Bernstein, P.L.C.

(57) ABSTRACT

In order to provide a hydrogen sensor for measuring a hydrogen concentration with high sensitivity and excellent mass-productivity, the hydrogen sensor includes: at least a first quartz vibrator and a second quartz vibrator formed in a quartz plate; a hydrogen reaction catalytic layer including a platinum film of platinum black formed on both sides of the first quartz vibrator; and a hydrogen non-reactive layer formed in the second quartz vibrator, wherein a hydrogen concentration is measured by measuring a temperature of the first quartz vibrator increasing by heat of combustion caused by oxidization of hydrogen by the hydrogen reaction catalytic layer as a change of a natural frequency of the first quartz vibrator with respect to a natural frequency of the second quartz vibrator.

4 Claims, 11 Drawing Sheets

(56) References Cited

U.S. PATENT DOCUMENTS

| | | | | |
|---|---|---|---|---|
| 4,879,005 A * | 11/1989 | Fray | ............... | G01N 27/4114 |
| | | | | 205/794.5 |
| 5,082,789 A * | 1/1992 | Morrison | ............... | G01N 27/12 |
| | | | | 422/94 |
| 6,029,500 A * | 2/2000 | Tom | ............... | G01N 29/036 |
| | | | | 310/313 R |
| 7,795,008 B2 * | 9/2010 | Dayagi | ............... | C07C 323/60 |
| | | | | 435/287.2 |
| 8,211,586 B2 | 7/2012 | Nakakubo | | |
| 8,249,811 B2 * | 8/2012 | Petrovic | ............... | G08B 29/183 |
| | | | | 702/1 |
| 2002/0142477 A1* | 10/2002 | Lewis | ............... | G01N 33/0031 |
| | | | | 436/151 |
| 2005/0279646 A1* | 12/2005 | Hasegawa | ............... | G01N 27/4166 |
| | | | | 205/789 |
| 2006/0090539 A1* | 5/2006 | Takahashi | ............... | G01N 33/24 |
| | | | | 73/19.09 |
| 2007/0117983 A1* | 5/2007 | Dayagi | ............... | C07C 323/60 |
| | | | | 546/153 |
| 2007/0235331 A1* | 10/2007 | Simpson | ............... | A61B 5/14546 |
| | | | | 204/403.01 |
| 2008/0038590 A1 | 2/2008 | Nakakubo | | |
| 2008/0057196 A1* | 3/2008 | Ishikawa | ............... | B01J 19/0093 |
| | | | | 427/248.1 |
| 2010/0025241 A1* | 2/2010 | Hane | ............... | G01N 27/4074 |
| | | | | 204/432 |
| 2010/0221148 A1 | 9/2010 | Oie et al. | | |
| 2013/0084474 A1* | 4/2013 | Mills | ............... | H01M 4/9016 |
| | | | | 429/9 |
| 2013/0260471 A1* | 10/2013 | Caron | ............... | G01N 33/0027 |
| | | | | 436/135 |
| 2015/0369778 A1* | 12/2015 | Fujii | ............... | G01N 29/022 |
| | | | | 506/9 |

FOREIGN PATENT DOCUMENTS

| | | |
|---|---|---|
| JP | 2008-224581 | 9/2008 |
| JP | 2008-233030 | 10/2008 |
| JP | 2008-275588 | 11/2008 |
| JP | 2008-292387 | 12/2008 |
| JP | 2009-42097 | 2/2009 |
| JP | 2010-256157 | 11/2010 |

* cited by examiner

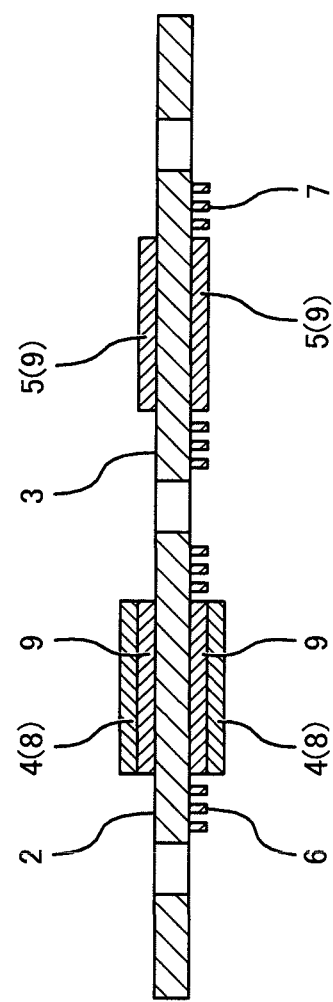

(a) Thickness = 116 nm (b) Thickness = 386 nm (c) Thickness = 518 nm

2 μm
(×5,000)

HYDROGEN SENSOR

FIELD OF THE INVENTION

The present invention relates to a hydrogen sensor for measuring a hydrogen concentration, and particularly to, a hydrogen sensor capable of providing high sensitivity and excellent mass-productivity.

BACKGROUND OF THE INVENTION

Hydrogen is attracting attention as an energy source to cope with environmental problems. That is, hydrogen is attracting attention as fuel of a fuel cell, fuel directly burned in an internal combustion engine, or the like. This is because of a characteristic that only water is generated even by burning hydrogen, and an energy density per weight is high. In addition, hydrogen can be easily obtained by electrolyzing water using electric energy such as a solar cell.

Meanwhile, since hydrogen is easily exploded by sparking or the like when it is mixed with oxygen, it is necessary to reliably detect leakage from a container such as a reservoir. That is, since hydrogen has a possibility of explosion when the concentration in the air exceeds 4%, a sensor for detecting this concentration with easiness in mass-production is demanded.

For this reason, as discussed in Patent Document 1, a hydrogen sensor has been developed, in which a hydrogen reaction catalytic layer is formed on a quartz crystal plate, and hydrogen is oxidized by the effect on the catalytic layer to generate heat, so that a temperature of the quartz crystal plate increases to change a natural frequency. The hydrogen concentration is measured by detecting the change of the natural frequency.

In the technique discussed in Patent Document 1, a hydrogen reaction catalytic layer is formed on a surface of a quartz vibrator, and a mass-production method is already established in the art, so that high practicality can be obtained.

In the technique discussed in Patent Document 2, the measurement value is stabilized, compared to the technique of Patent Document 1. That is, a hydrogen reaction catalytic layer is formed on one side or both sides of a fourth region of the quartz plate, and a hydrogen non-reactive layer is formed similarly in the fifth region of the surface of the quartz plate. In addition, hydrogen is oxidized by the hydrogen reaction catalytic layer to generate heat of combustion, and a change of the natural frequency of the first quartz vibrator of the quartz plate caused by the heat of combustion is measured on the basis of the natural frequency of the fifth region of the quartz plate, so that the hydrogen concentration is measured on the basis of the change of the natural frequency.

CITATION LIST

Patent Documents

Patent Document 1: JP 2008-224581 A Patent Document 2: JP 2010-256157 A

SUMMARY OF THE INVENTION

Problems to be Solved by the Invention

However, in the hydrogen sensor of the prior art discussed in Patent Document 1 described above, a temperature of the quartz vibrator increases by the heat generated from the hydrogen reaction catalytic layer, and the hydrogen concentration is measured on the basis of the temperature change. Therefore, a measurement value may change depending on a temperature of the used environment.

In the technique discussed in Patent Document 2, the measurement value is stable even for a change of the atmospheric temperature, but there is a demand for a sensor having higher sensitivity. Meanwhile, it is also necessary to satisfy a demand for preventing a decrease of mechanical strength of the quartz vibrator against a shock that may be caused by increasing the sensitivity or a demand for improving mass-productivity.

In view of the aforementioned problems, it is therefore an object of the present invention to provide a hydrogen sensor in which an error in measurement data is less generated even by an environmental temperature itself or a change of the environmental temperature, sensitivity is high, there is no degradation in mechanical strength even by increasing sensitivity, and mass-productivity is excellent.

Means for Solving the Problem

According to an aspect of the invention, there is provided a hydrogen sensor including: at least a first quartz vibrator and a second quartz vibrator formed in a quartz plate; a hydrogen reaction catalytic layer including a platinum film of platinum black formed on both sides of the first quartz vibrator; and a hydrogen non-reactive layer formed in the second quartz vibrator, wherein a hydrogen concentration is measured by measuring a temperature of the first quartz vibrator increased by heat of combustion caused by oxidization of hydrogen by the hydrogen reaction catalytic layer as a change of a natural frequency of the first quartz vibrator with respect to a natural frequency of the second quartz vibrator.

According to another aspect of the invention, there is provided a hydrogen sensor including: at least a first quartz vibrator and a second quartz vibrator formed in a quartz plate; a hydrogen reaction catalytic layer that is formed on both sides of the first quartz vibrator and includes a platinum film having a plurality of protrusions on its surface, the protrusions having a particulate shape in surface observation or having a dendritic shape, a needle-like shape, or a columnar shape in cross-sectional observation; and a hydrogen non-reactive layer formed in the second quartz vibrator, wherein a hydrogen concentration is measured by measuring a temperature of the first quartz vibrator increased by heat of combustion caused by oxidization of hydrogen in the hydrogen reaction catalytic layer as a change of a natural frequency of the first quartz vibrator with respect to a natural frequency of the second quartz vibrator.

Advantageous Effect of the Invention

In the hydrogen sensor according to the present invention, the first quartz vibrator and second quartz vibrator are formed in the quartz plate, the hydrogen reaction catalytic layer of platinum black is formed in the first quartz vibrator, and the hydrogen non-reactive layer is formed in the second quartz vibrator as described above. Alternatively, the first quartz vibrator has the hydrogen reaction catalytic layer including the platinum film having a plurality of protrusions on its surface, and the protrusions have a particulate shape in surface observation, or have a dendritic, needle-like, or columnar shape in cross-sectional observation.

According to the present invention, the hydrogen reaction catalytic layer of the first quartz vibrator generates heat by influence of the heat of combustion of hydrogen generated as it comes into contact with gas such as air containing hydrogen. In this case, since the first quartz vibrator and second quartz vibrator are influenced by the heat other than the heat of combustion under the same condition, it is possible to exclude influence caused by factors other than the heat of combustion of hydrogen by calculating a frequency difference or ratio between the first quartz vibrator and second quartz vibrator or combining them. For this reason, it is possible to accurately measure the hydrogen concentration even when the environmental temperature changes. In addition, according to the present invention, it is possible to improve sensitivity, compare to the prior art.

Since each region of the quartz plate is identical as discussed in Patent Document 2, mechanical strength does not decrease by improving the sensitivity. In addition, the hydrogen reaction catalytic layer may be formed through electroplating, which is not particularly difficult. Therefore, it is possible to provide excellent mass-productivity.

BRIEF DESCRIPTION OF DRAWINGS

FIG. 5 is a cross-sectional view illustrating the hydrogen sensor of FIGS. 3 and 4;

DESCRIPTION OF EMBODIMENTS

Embodiments of the present invention (hereinafter, referred to as "this embodiment") will now be described in details. Note that the invention is not limited to the following embodiments, and various modifications may be possible without departing from the scope of the subject matter.

First Embodiment

Figure 1:
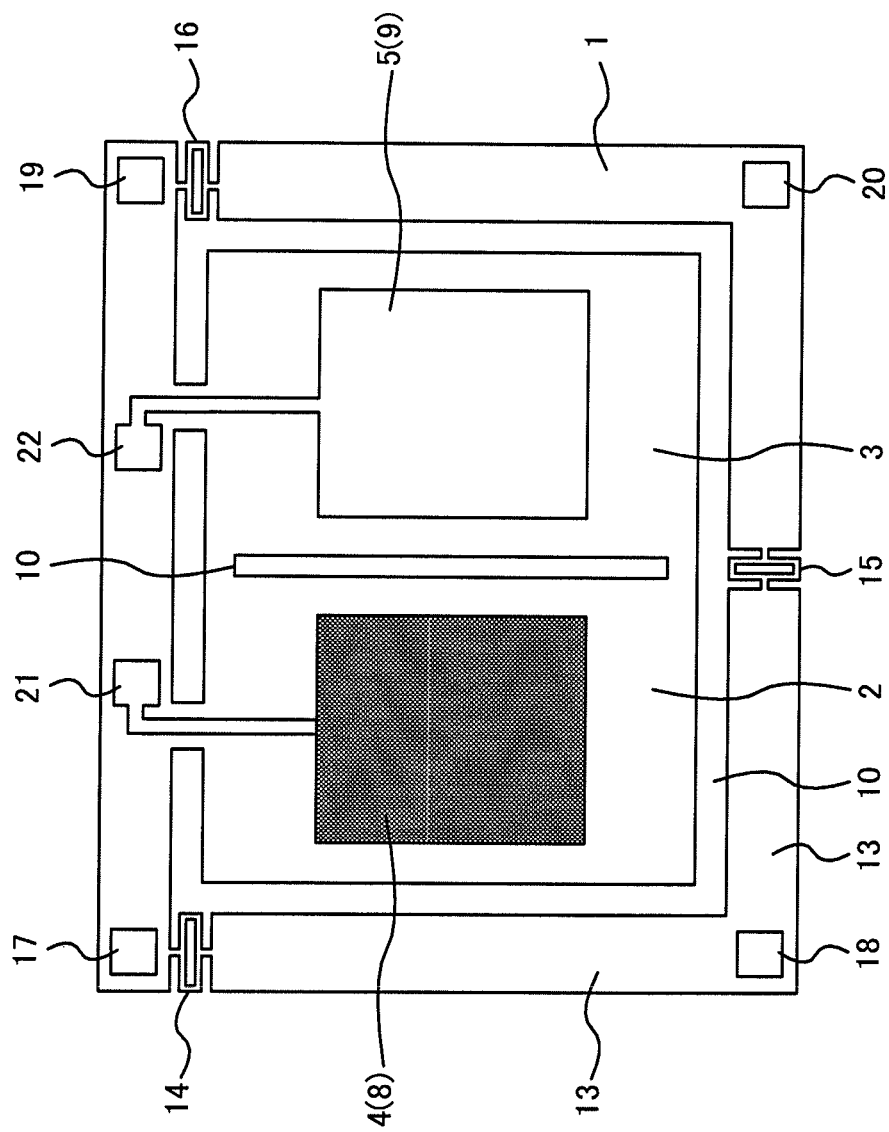
FIG. 1 is a front surface layout illustrating a hydrogen sensor according to a first embodiment of the invention.
Figure 2:
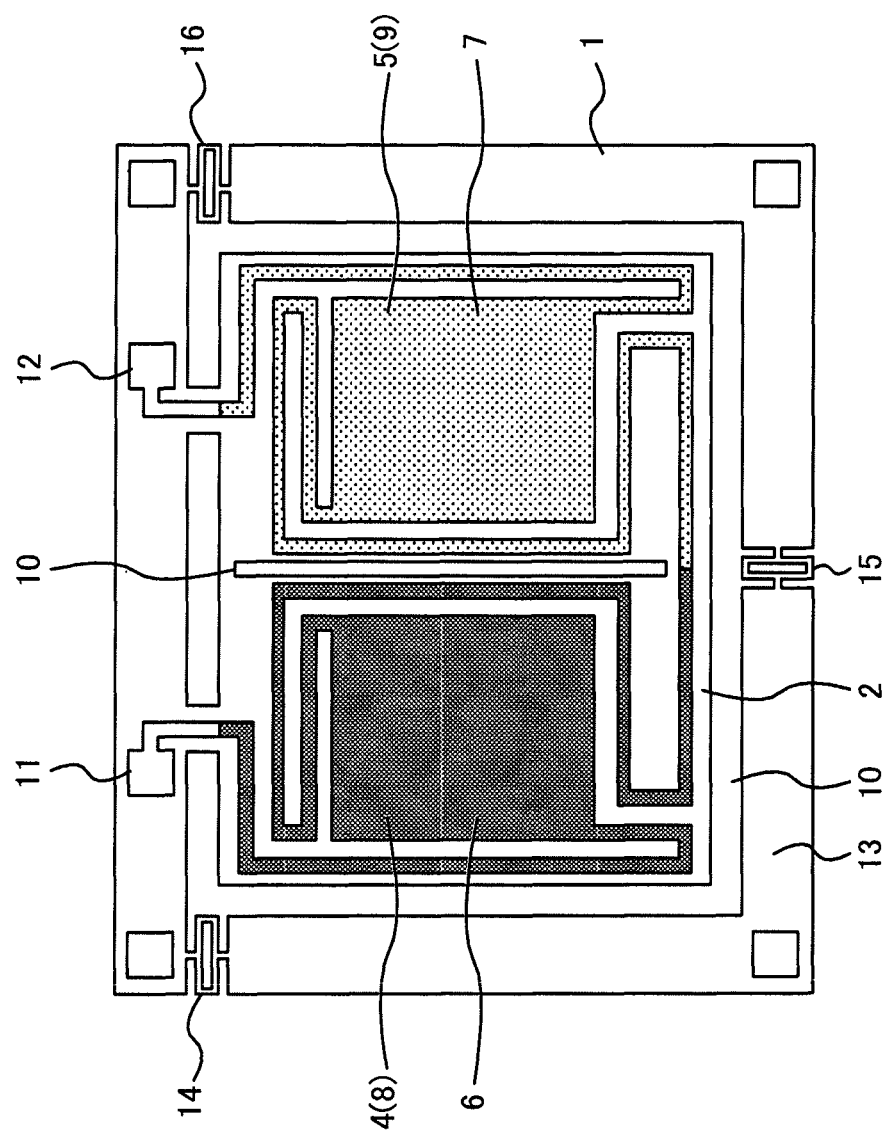
FIG. 2 is a rear surface layout illustrating the hydrogen sensor according to the first embodiment of the invention.

A hydrogen sensor according to a first embodiment will now be described in details with reference to the accompanying drawings. FIG. 1 is a front surface layout illustrating a hydrogen sensor according to the first embodiment of the invention. FIG. 2 is a rear surface layout illustrating the hydrogen sensor according to the first embodiment of the invention. Note that, although the left and right sides of the rear surface layout of FIG. 2 are reversed by inverting the front surface layout of FIG. 1, the rear surface layout of FIG. 2 is illustrated such that the left and right sides are not reversed for easy understanding purposes.

Element 1 of FIGS. 1 and 2 is a quartz plate (quartz substrate) fabricated by cutting quartz crystals through etching or the like. Element 2 is a first quartz vibrator, and Element 3 is a second quartz vibrator.

As illustrated in FIGS. 1 and 2, the first quartz vibrator 2 has a hydrogen reaction catalytic layer 4 on both sides of a quartz piece formed by cutting the quartz plate 1. The hydrogen reaction catalytic layer 4 includes a platinum film 8. The hydrogen reaction catalytic layer 4 functions as an electrode of the first quartz vibrator 2.

As illustrated in FIGS. 1 and 2, the second quartz vibrator 3 has a hydrogen non-reactive layer 5 on both sides of the quartz piece formed by cutting the quartz plate 1. The hydrogen non-reactive layer 5 is formed of, for example, a gold film 9. The hydrogen non-reactive layer 5 functions as an electrode of the second quartz vibrator 3.

A platinum film 8 will be described. The platinum film 8 is formed of platinum black. Here, "platinum black" is a platinum film appearing in black on its surface and is known as a strong oxidation-reduction catalyst. However, in this embodiment, the surface does not necessarily have a black color, and the "platinum black" may also have either a gray color or a color close to gray.

The surface of the platinum film 8 is roughened, or is formed of a porous material, so that an actual surface area is much larger than the apparent surface area.

Such a platinum film 8 appears as described below in the scanning electron microscope (SEM) photograph.

Specifically, the platinum film 8 has a plurality of protrusions on the surface, and the protrusions have a particulate shape as seen in surface observation. In cross-sectional observation, the protrusions have a dendritic, needle-like, or columnar shape. Here, the "particulate shape" refers to a shape appearing in the SEM photograph as a dot or lump to which one or a plurality of particles are adhered. In addition, the "dendritic shape" refers to a branched shape, and the "needle-like shape" refers to a pointed tip shape. The "columnar shape" refers to any irregular protrusion shape other than the "dendritic shape" and the "needle-like shape". Note that a real SEM photograph will be described below.

The platinum film 8 is necessary to have a temperature at a certain level or more in order to exert a catalytic action. For this reason, as illustrated in FIG. 2, a heater wire 6 for heating is formed on the back side of the quartz plate 1 to match a position of the hydrogen reaction catalytic layer 4.

As illustrated in FIG. 2, the heater wire 7 for heating is also formed in a position matching the hydrogen non-reactive layer 5 on the back side of the quartz plate 1. In addition, the heater wires 6 and 7 are formed to have the same property. This is because a heat amount generated from the hydrogen reaction catalytic layer 4 is accurately detected by heating both the hydrogen reaction catalytic layer 4 and the hydrogen non-reactive layer 5 under the same condition.

As illustrated in FIG. 2, the heater wires 6 and 7 are integrally formed of the same material.

Element 10 of FIGS. 1 and 2 is a slit formed in the quartz plate 1. By means of this slit 10, the heat influence is suppressed between the first quartz vibrator 2 and second quartz vibrator 3. Note that Elements 11 and 12 are terminals for supplying power to the heater wires 6 and 7, respectively.

Element 13 is an outer frame that surrounds an outer side of the first quartz vibrator 2 and second quartz vibrator 3, and the outer frame 13 includes, for example, three spring portions 14 to 16. In addition, the first quartz vibrator 2 and second quartz vibrator 3 are separated from the outer frame 13 by the slit 10 by excluding some parts. By providing the outer frame 13 and the spring portions 14 to 16 in this manner, it is possible to form a structure resisting to a stress in the first quartz vibrator 2 and second quartz vibrator 3 even when a stress is applied to the outer frame 13.

Elements 21 and 22 of FIG. 1 are terminals connected to an oscillation circuit such as a Colpitts oscillator for measuring a resonant frequency of the first quartz vibrator 2 (however, a quartz-based oscillation circuit is generally known in the art, and will not be described herein). In addition, the oscillation circuit is connected to a frequency measurement device. The frequency measurement circuit is also generally known in the art, and will not be described herein.

The hydrogen sensor of Example 1 is formed in the aforementioned configuration. Operations of the hydrogen sensor and how to use it will now be described. The quartz plate 1 is mounted on a suitable substrate and is packaged in a casing for modularization in order to prevent it from being mechanically damaged. This casing has, for example, an opening for allowing gases to sufficiently flow. Since the substrate and the casing described above may be those commonly used in electronic parts, they are not technically distinctive, and are not illustrated for simplicity purposes.

First, power is fed to the heater wires 6 and 7 through the terminals 11 and 12. By virtue of this feeding, the first quartz vibrator 2 and second quartz vibrator 3 are preheated under the same condition. Here, the preheating refers to a process of increasing the temperature of the hydrogen reaction catalytic layer 4 such that it can function as a catalyst.

The terminal 21 and a terminal on the back side (not shown) are connected to the oscillation circuit. Then, the quartz plate 1 vibrates as a thickness shear vibrator, and the oscillation circuit oscillates at its natural frequency. Since the oscillation frequency of the oscillation circuit is measured by the frequency measurement device, the resonant frequency of the first quartz vibrator 2 is measured. In addition, the terminal 22 and a terminal of the back side (not shown) are connected to the oscillation circuit, and the oscillation frequency of the oscillation circuit is measured by the frequency measurement device, so that the resonant frequency of the second quartz vibrator 3 is measured.

Note that the terminals 17, 18, 19, and 20 are pads for fixing the hydrogen sensor to a package (not shown).

Here, the resonant frequencies of the first quartz vibrator 2 and second quartz vibrator 3 are measured while they have high temperatures through preheating.

In this state, as the air containing hydrogen flows, the hydrogen is oxidized by oxygen in the air by virtue of a catalytic action of the hydrogen reaction catalytic layer 4 of the hydrogen sensor. In response to this oxidation, heat of combustion is generated, so that the temperature of the first quartz vibrator 2 increases over the preheating temperature.

The second quartz vibrator 3 includes the hydrogen non-reactive layer 5, so that hydrogen is not oxidized even when the air contains hydrogen. In addition, the temperature of the second quartz vibrator 3 is maintained at the preheating temperature. That is, while the first quartz vibrator 2 has a temperature equal to or higher than the preheating temperature by virtue of the heat of combustion of hydrogen, the second quartz vibrator 3 has a temperature maintained at the preheating temperature. Therefore, while the first quartz vibrator 2 has a resonant frequency generated at a temperature that depends on the preheating temperature and the temperature increase caused by the heat of combustion of hydrogen, the second quartz vibrator 3 has a resonant frequency generated at the preheating temperature.

Here, it is possible to eliminate a factor corresponding to the temperature increase caused by the preheating and purely detect only a factor of the frequency change influenced by the heat of combustion of hydrogen by measuring the resonant frequencies of the first quartz vibrator 2 and second quartz vibrator 3 and taking a difference therebetween.

In this manner, a hydrogen concentration in the air can be measured by measuring a frequency change caused by the heat of combustion of hydrogen.

Second Embodiment

Figure 3:
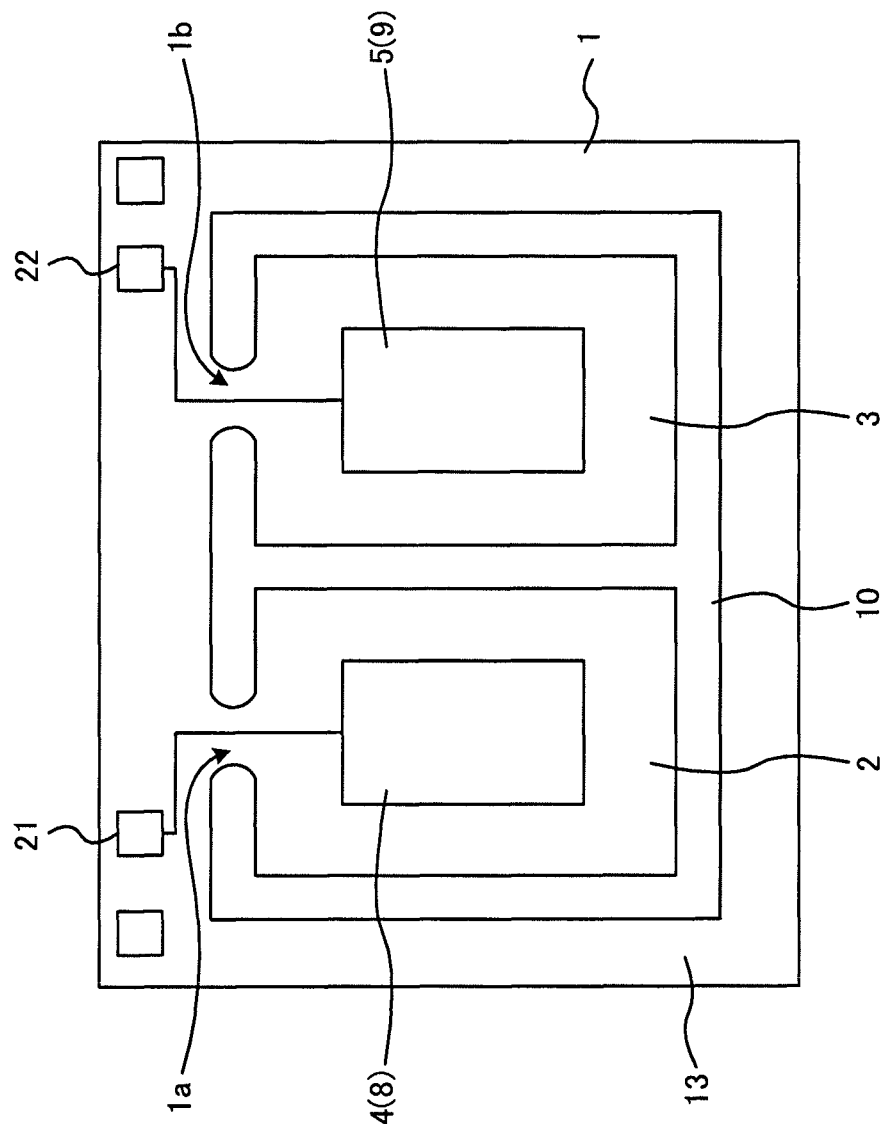
FIG. 3 is a front surface layout illustrating the hydrogen sensor according to the second embodiment of the invention.
Figure 4:
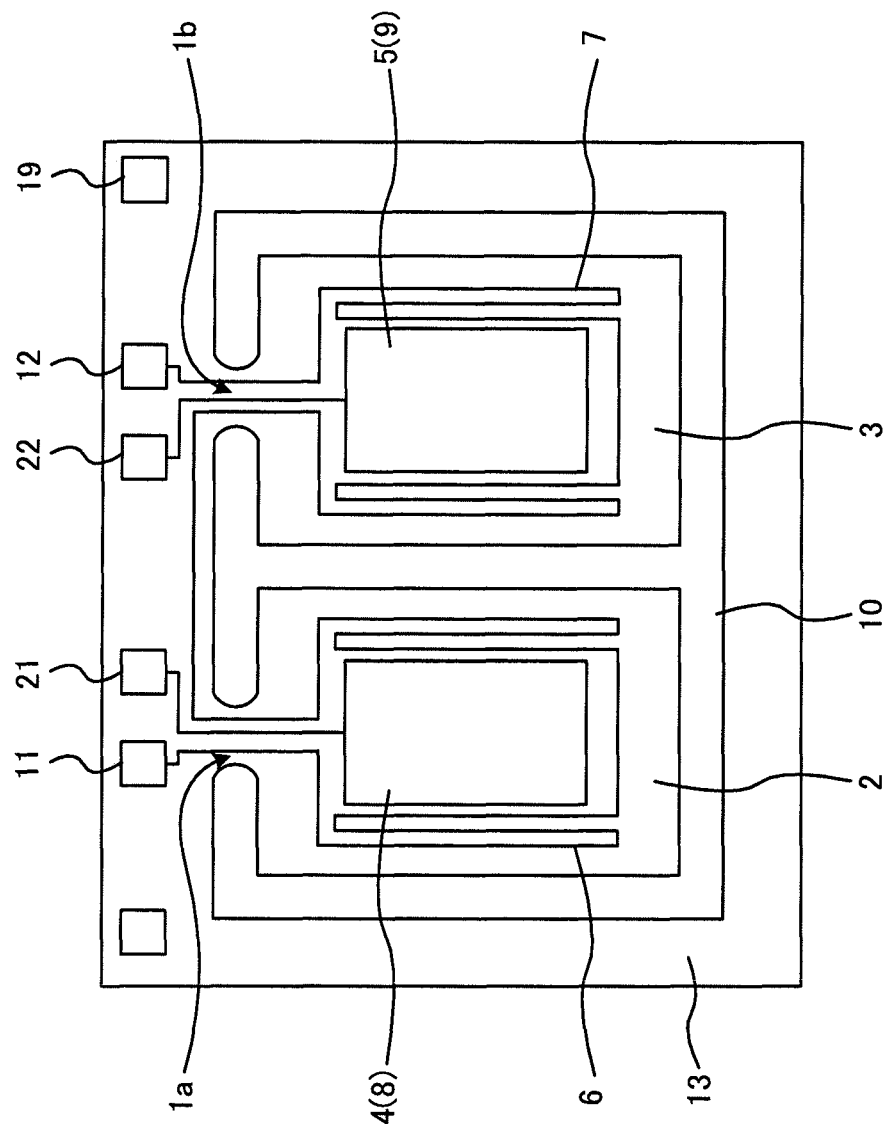
FIG. 4 is a rear surface layout illustrating the hydrogen sensor according to the second embodiment of the invention.

FIG. 3 is a front surface layout illustrating a hydrogen sensor according to a second embodiment of the invention. FIG. 4 is a rear surface layout illustrating the hydrogen sensor according to the second embodiment of the invention. FIG. 5 is a cross-sectional view illustrating the hydrogen sensor of FIGS. 3 and 4. Note that, although the left and right sides of the rear surface layout of FIG. 4 are reversed by inverting the front surface layout of FIG. 3, the rear surface layout of FIG. 4 is illustrated such that the left and right sides are not reversed for easy understanding purposes. In FIGS. 3 and 4, like reference numerals denote like elements as in FIGS. 1 and 2, and will not be described herein.

The hydrogen sensor of FIGS. 3 and 4 has a first quartz vibrator 2 and a second quartz vibrator 3, which are separated from each other by a slit 10. In addition, the slit 10 separates the first quartz vibrator 2 and second quartz vibrator 3 from the outer frame 13 by leaving a part of the outer frame 13.

As illustrated in FIGS. 3 and 4, the first quartz vibrator 2 has a cantilevered structure connected to the outer frame 13 by interposing a connecting portion 1a. Similarly, the second quartz vibrator 3 has a cantilevered structure connected to the outer frame 13 by interposing a connecting portion 1b.

As illustrated in FIGS. 3 and 4, a hydrogen reaction catalytic layer 4 including a platinum film 8 is formed in a center of the first quartz vibrator 2. The hydrogen reaction catalytic layer 4 is formed on both sides of the first quartz vibrator 2. In addition, a hydrogen non-reactive layer 5 including a gold film 9 is formed in a center of the second quartz vibrator 3. The hydrogen non-reactive layer 5 is formed on both sides of the second quartz vibrator 3.

As illustrated in FIG. 5, the gold film 9 is formed as a first layer on both sides of the first quartz vibrator 2, similar to the second quartz vibrator 3. The hydrogen reaction catalytic layer 4 including the platinum film 8 is formed by overlapping with the surface of the gold film 9. Note that, although not shown in the drawings, a chromium (Cr) layer is formed as a base layer of the gold film 9.

As illustrated in FIG. 4, the heater wire 6 is provided around the hydrogen reaction catalytic layer 4 on the back sides of the first quartz vibrator 2 and second quartz vibrator 3, and the heater wire 7 is provided around the hydrogen non-reactive layer 5. Each of the heater wires 6 and 7 is connected and integrated in the position of the outer frame 13 through the connecting portions 1a and 1b.

The heater wires 6 and 7 may be formed simultaneously with formation of the pattern of the gold film 9 or may be formed in a separate process. The heater wires 6 and 7 may be formed of a Cr/Au lamination film or other lamination films (note that chromium (Cr), nickel (Ni), titanium (Ti), or the like are necessary as an adhesive layer of the quartz plate 1) without limiting to materials.

As illustrated in FIG. 4, by having the heater wires 6 and 7 meander around the hydrogen reaction catalytic layer 4 and the hydrogen non-reactive layer 5, it is possible to improve heating efficiency.

Similar to the first embodiment, according to the second embodiment of FIGS. 3 and 4, the platinum film 8 is formed of platinum black.

Alternatively, the platinum film 8 has a plurality of protrusions on the surface, and the protrusions have a particulate shape in surface observation. Alternatively, the protrusions have a dendritic, needle-like, or columnar shape in cross-sectional observation.

In the prior art, the hydrogen reaction catalytic layer 4 includes a glossy platinum film formed by platinum (Pt) sputtering. However, according to this embodiment, the hydrogen reaction catalytic layer 4 includes a platinum film having a three-dimensional nanostructure. Specifically, the hydrogen reaction catalytic layer 4 is formed of platinum black. As a result, it is possible to remarkably improve sensitivity.

According to this embodiment, a surface state of the platinum film 8 can be observed on the SEM photograph.

In this embodiment, the surface and the cross section were observed using a scanning electron microscope (SEM, Model No. S-3400N, manufactured by Hitachi High-Technologies Corporation). As an SEM observation condition, an accelerating voltage was set to 30 kV, and an observation magnification ratio was set to 5,000.

Figure 6A:
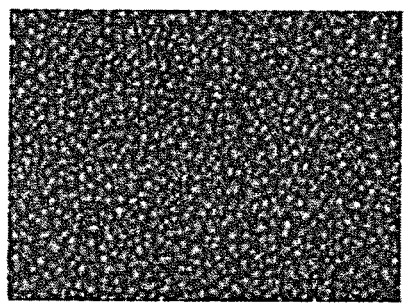
FIGS. 6A to 6C are scanning electron microscope (SEM) photographs obtained by observing surfaces of hydrogen reaction catalytic layers having different thicknesses of the hydrogen sensor according to the invention.
Figure 6B:
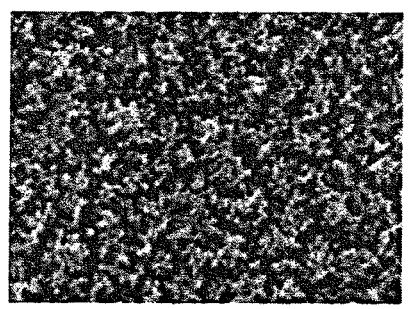
Figure 6C:
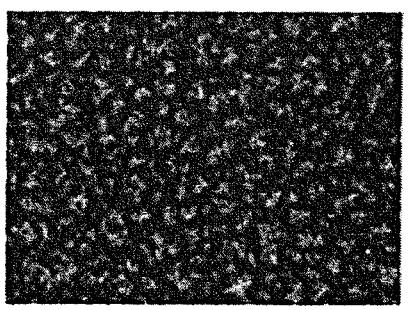
Figure 7:
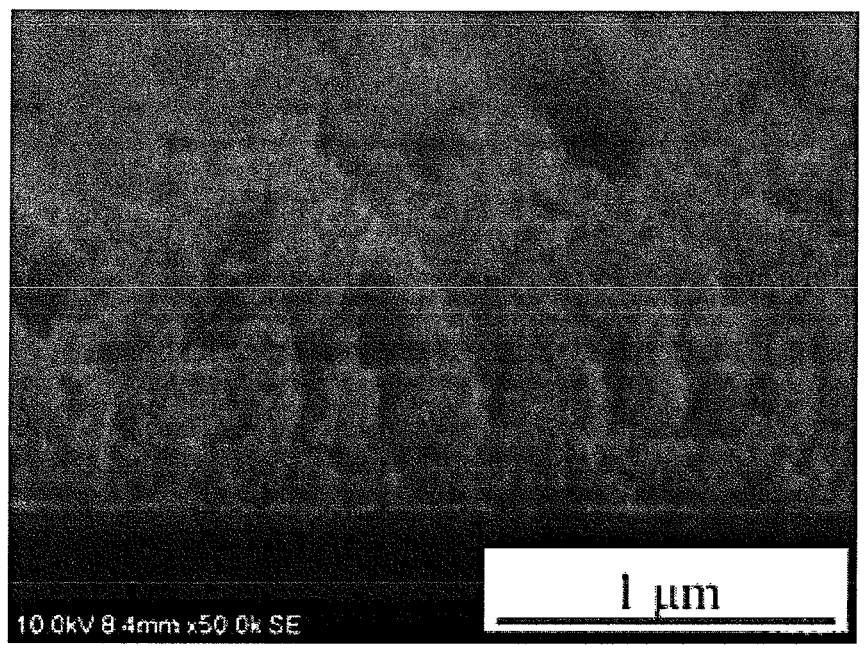
FIG. 7 is an SEM photograph obtained by observing a cross section of the hydrogen reaction catalytic layer of the hydrogen sensor according to the invention.
Figure 8A:
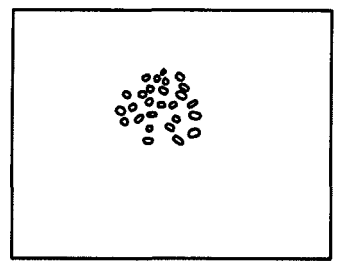
FIGS. 8A to 8C are schematic diagrams partially illustrating the SEM photographs of FIGS. 6A to 6C, respectively.
Figure 8B:
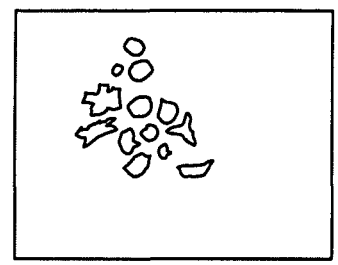
Figure 8C:
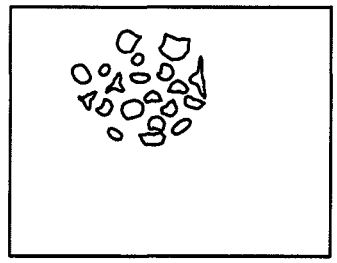
Figure 9:
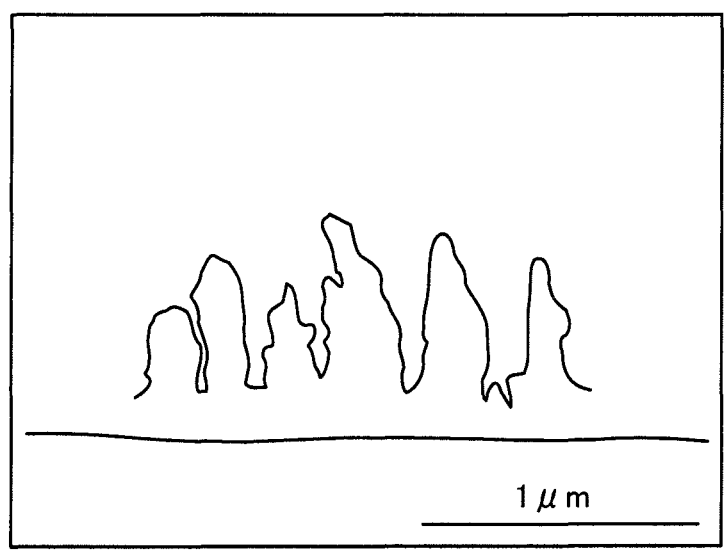
FIG. 9 is a schematic diagram partially illustrating the SEM photograph of FIG. 7.

FIGS. 6A to 6C are SEM photographs obtained by observing the surface of the hydrogen reaction catalytic layer of the hydrogen sensor according to the present invention at different thicknesses. FIG. 7 is an SEM photograph obtained by observing a cross section of the hydrogen reaction catalytic layer of the hydrogen sensor according to the present invention. FIGS. 8A to 8C are schematic diagrams partially illustrating the SEM photographs of FIGS. 6A to 6C, respectively. FIG. 9 is a schematic diagram partially illustrating the SEM photograph of FIG. 7.

The upper left SEM photograph of FIG. 6A is a surface photograph of a platinum black plating film having an average thickness of 116 nm. The upper right SEM photograph of FIG. 6B is a surface photograph of a platinum black plating film having an average thickness of 386 nm. The lower SEM photograph of FIG. 6C is a surface photograph of a platinum black plating film having an average thickness of 518 nm.

Here, the "average thickness" is measured using the following method. That is, measurement is performed on five arbitrary places on the surface of the platinum film by employing a laser microscope VK-X210 manufactured by KEYENCE as the measuring device, so that an average value of them is taken as the average thickness.

FIGS. 8A to 8C schematically illustrate only parts of the surface photographs of FIGS. 6A to 6C. As illustrated in FIGS. 6A to 6C and 8A to 8C, in the platinum film having an average thickness of 116 nm, the white portions in the SEM observation are protrusions having a particulate shape protruding from the surface. In addition, the dark portions around the white portions have a gray color. It was recognized that, in these portions, the thickness of the platinum film was thin, so that the underlying Au were seen therethrough.

As illustrated in FIGS. 6A to 6C and 8A to 8C, it was recognized that, in the platinum film having an average thickness of 116 nm, a plurality of protrusions having a particulate shape were scattered.

In the platinum film having an average thickness of 386 nm, as illustrated in FIG. 6B, the dark portions around the particulate protrusions appearing in white had a dark gray color which was darker than that of the platinum film having an average thickness of 116 nm.

In the platinum film having an average thickness of 518 nm, as illustrated in FIG. 6C, the dark portions around the particulate protrusions appearing in white had a black color which was further darker than that of the platinum film having an average thickness of 386 nm.

Subsequently, the SEM cross section will be described. The average thickness of the platinum films of FIGS. 7 and 8A to 8C were approximately 500 nm. As illustrated in FIGS. 7 and 8A to 8C, a plurality of protrusions were observed in the SEM cross section and had irregular shapes. As a shape of the protrusions, a dendritic shape, a needle-like shape, or any irregular shape other than the dendritic and needle-like shapes (these will be referred to as a "columnar shape" herein) were recognized.

As illustrated in FIGS. 7 and 8A to 8C, each protrusion had a large aspect ratio (maximum height/maximum width) such as approximately 2 to 10.

According to this embodiment, the platinum film 8 preferably has an average thickness of 30 nm or larger and 600 nm or smaller. However, when the average thickness of the platinum film 8 is too thin, film formation becomes difficult. Therefore, the average thickness is preferably set to 30 nm or larger. Meanwhile, when the average thickness of the platinum film 8 is too large, the embossing on the surface of the platinum film 8 is reduced, and the surface area is reduced. Therefore, the average thickness is preferably set to 600 nm or smaller.

The average thickness of the platinum film 8 is preferably set to 50 nm or larger and 500 nm or smaller, more preferably 70 nm or larger and 300 nm or smaller, still more preferably 70 nm or larger and 150 nm or smaller, and most preferably approximately 100 nm.

A method of manufacturing the hydrogen sensor according to this embodiment will now be described. FIGS. 10A to 10E are cross-sectional views illustrating a process of manufacturing the hydrogen sensor according to this embodiment. Note that, in FIGS. 10A to 10E, the back side of the hydrogen sensor is illustrated in the upper side in each manufacturing process.

Figure 10A:
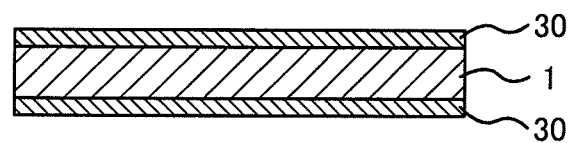
FIGS. 10A to 10E are cross-sectional views illustrating a manufacturing process of the hydrogen sensor according to an embodiment of the invention.

In the process of FIG. 10A, a Cr/Au film 30 is formed on both sides of the quartz plate (quartz substrate) 1 through sputtering.

Figure 10B:
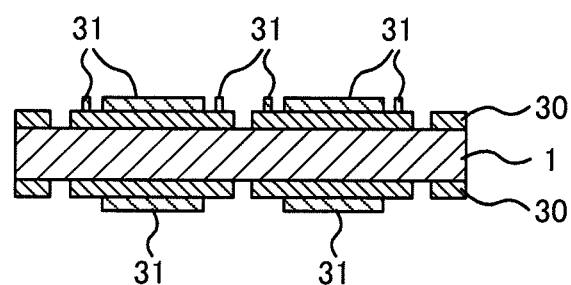

Subsequently, the Cr/Au film 30 is formed by photolithography except for the portions corresponding to the slit 10, and a resist pattern 31 is formed on the surface of the Cr/Au film 30 as illustrated in FIG. 10B. This resist pattern 31 includes shape patterns of the hydrogen reaction catalytic layer 4 and the hydrogen non-reactive layer 5 of FIGS. 3 and 4, shape patterns of the heater wires 6 and 7, and shape patterns of various wires.

Subsequently, in the process of FIG. 10C, the exposed portions of the quartz plate 1 are etched and removed in order to form the slit 10. By forming the slit 10, the first quartz vibrator 2 and second quartz vibrator 3 can be separated from each other and can be isolated from the outer frame 13 by excluding some parts as illustrated in FIGS. 3 and 4.

Figure 10C:
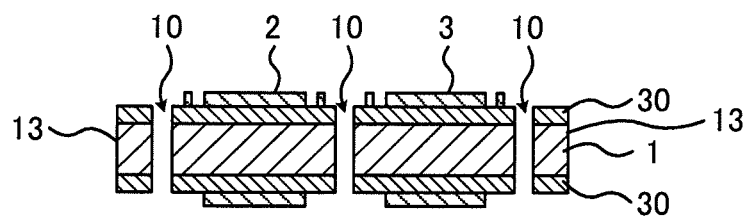
Figure 10D:
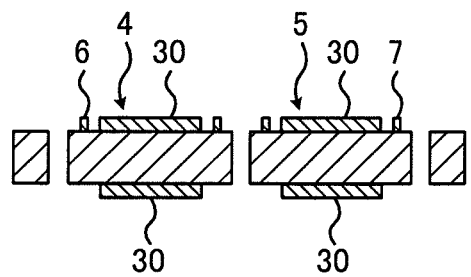

Then, in the process of FIG. 10D, the Cr/Au film 30 not covered by the resist pattern 31 of FIG. 10C is removed through etching. As a result, it is possible to allow the Cr/Au film 30 to remain in the shape patterns of the hydrogen reaction catalytic layer 4 and the hydrogen non-reactive layer 5, the shape patterns of the heater wires 6 and 7, and the shape patterns of various wires.

Figure 10E:
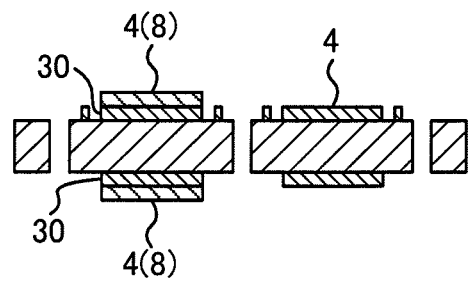

Then, in the process of FIG. 10E, the platinum film 8 is plated on the surface of the Cr/Au film 30 in the center of the first quartz vibrator 2, so as to form the hydrogen reaction catalytic layer 4 including the platinum film 8. Note that a mask is not particularly necessary as long as the platinum film 8 can be selectively plated during the plating.

Figure 11:
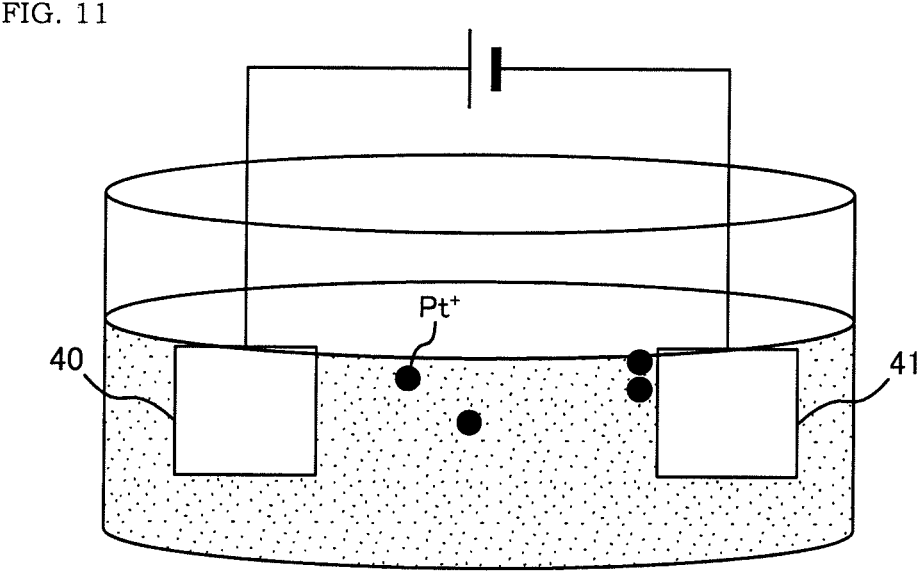
FIG. 11 is a perspective view illustrating a process of forming the hydrogen reaction catalytic layer of the hydrogen sensor according to an embodiment of the invention.

A method of forming the hydrogen reaction catalytic layer 4 including the platinum film 8 will now be described. FIG. 11 is a perspective view illustrating the process of forming the hydrogen reaction catalytic layer of the hydrogen sensor according to this embodiment. As illustrated in FIG. 11, a positive electrode 40 has a platinum (Pt) plate, and a negative electrode 41 has a quartz wafer (in a state illustrated in FIG. 10D). Here, in FIG. 11, a single positive electrode 40 is illustrated. However, preferably, a pair of positive electrodes 40 are provided, and both sides of the negative electrode 41 are interposed between the positive electrodes 40. As a result, it is possible to plate the platinum film on both sides of the quartz water in a single process and to uniformize the thicknesses of the platinum films formed on the both sides.

As a solution, for example, hexachloroplatinic (IV) acid hexahydrate ($H_2[PtCl_6] \cdot 6H_2O$) of 3 g, and lead acetate (III) trihydrate $Pb(CH_3COO)_2 \cdot 3H_2O$ of 0.06 g were dissolved in super pure water to form a plating bath.

The surface state and the thickness of the platinum film depend on the current density and time. According to this embodiment, the current density is preferably set to 4 mA/cm$^2$ or higher, more preferably 5.0 mA/cm$^2$ or higher, and still more preferably 5.5 mA/cm$^2$ or higher. An upper limit of the current density is set to approximately 12 mA/cm$^2$, and preferably approximately 10 mA/cm$^2$. In addition, the plating time is set to, for example, 300 sec or shorter, preferably 100 sec or shorter, and more preferably approximately several tens of seconds. As a result, appearance has a gray state called platinum gray or platinum black. In this manner, in the platinum gray or platinum black state, it is possible to enlarge embossing on the platinum film and obtains a complicated structure (such as a dendritic protrusion) in the SEM cross section.

As a result, it is possible to selectively plate the platinum film 8 only in the first vibrator 2 using the hydrogen reaction catalytic layer 4 after formation of the sensor. According to this embodiment, patterning can be appropriately applied to electrodes on both sides of the first vibrator 2. In addition, it is possible to easily control the thickness of the platinum film 8. Furthermore, advantageously, it is possible to collectively plate all of samples on the wafer.

Alternatively, in this embodiment, platinum black powder may be coated on electrodes of both sides of the first vibrator 2 using a binder. In this case, an inorganic binder is preferably employed as the binder.

EXAMPLES

Examples performed to prove the effects of the present invention will now be described. Note that the present invention is not limited to any one of the following examples.

Experimental Example 1

In an experiment, a hydrogen sensor as an example was manufactured by forming the hydrogen reaction catalytic layer 4 by plating platinum black, and a hydrogen sensor of a comparative example was manufactured by sputtering platinum as discussed in Patent Document 2. Then, sensitivity of each hydrogen sensor was measured under a hydrogen environment. A result of the experiment is illustrated in FIG. 12.

Figure 12:
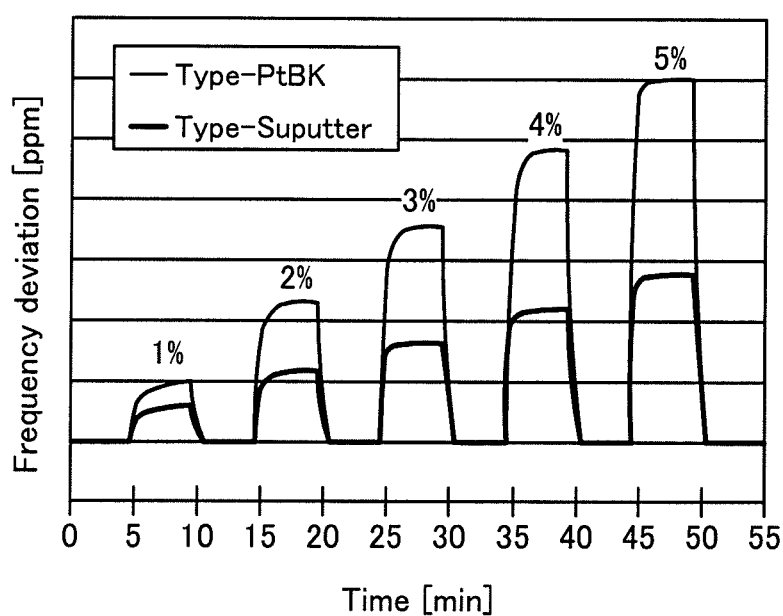
FIG. 12 is a graph illustrating a characteristic of the hydrogen sensor according to the invention.

As illustrated in FIG. 12, it was recognized that the hydrogen sensor of the example had sensitivity nearly double that of the hydrogen sensor of the comparative example.

As another experiment of the sensitivity, a vibrator (hydrogen sensor) having a platinum film having an average thickness of 518 nm was manufactured by plating platinum black at a current density of 9.17 mA/cm$^2$. In addition, as a comparative example, a vibrator (hydrogen sensor) having a platinum sputtering film having a thickness of 250 nm was manufactured.

For sensitivity measurement, a pure air-hydrogen gas mixture having a hydrogen concentration of 0.3% was employed. The result of the sensitivity measurement is shown in Table 1 as follows.

TABLE 1

| Type of platinum catalyst | Pt sputtering | Pt-black plating |
| --- | --- | --- |
| Number of samples | 4 | 3 |
| Frequency difference [ppm] | 40.2 | 146.6 |
| Sensitivity [ppm/%] | 134.1 | 488.7 |
| Standard deviation of sensitivity | 9.5 | 82.1 |
| TCF [ppm/° C.] | 20 | 26.3 |
| ΔT[° C.] @ H$_2$: 1% | 6.7 | 18.8 |

As shown in Table 1, for a resonance frequency of approximately 16 MHz, an average increase of 146.6 ppm in frequency was observed in the hydrogen sensor as an example having the platinum black plating. This is 3.65 times higher sensitivity than that of the hydrogen sensor of the comparative example having the platinum sputtering film. The increase of temperature caused by a combustion reaction of hydrogen was calculated using the actual measurement value of the temperature coefficients of frequency (TCF) of the hydrogen sensor. As a result, it was recognized that the increase of temperature in the hydrogen sensor of the example having the platinum black plating was 2.8 times that of the hydrogen sensor of the comparative example having the platinum sputtering film. In this manner, it was recognized that, in the hydrogen sensor of the example having the platinum black plating, the TCF increased, and this led to improvement of the sensitivity of the hydrogen sensor over the difference of the platinum catalyst.

Experimental Example 2

Next, Q-factors were measured using each hydrogen sensor using the hydrogen reaction catalytic layer 4 having platinum films having different thicknesses as illustrated in FIGS. 6A to 6C. Resultant values are shown in FIG. 13.

Figure 13:
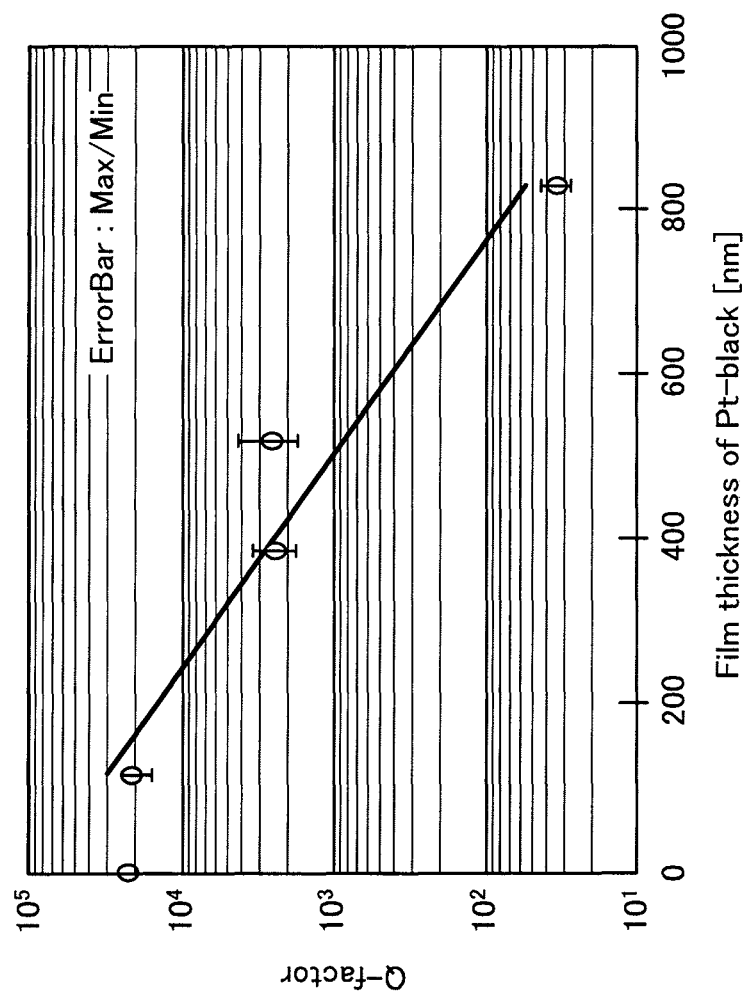
FIG. 13 is a graph illustrating a characteristic of the hydrogen sensor according to the invention.

Data obtained by setting "thickness=0 nm" of FIG. 13 is a Q-factor of the vibrator prior to platinum film plating. As illustrated in FIG. 13, it was recognized that the Q-factor was exponentially reduced relative to the thickness of the platinum film.

As illustrated in FIG. 13, it was recognized that the Q-factor of the vibrator having a platinum film thickness of approximately 100 nm was nearly equal to that of the vibrator prior to formation of the platinum film (thickness=0 nm).

In this manner, it was recognized that reduction of the Q-factor could be suppressed. The thickness of the platinum film is preferably set to 600 nm or smaller, more preferably 500 nm or smaller, further more preferably 300 nm or smaller, still more preferably 150 nm or smaller, and most preferably approximately 100 nm.

Experimental Example 3

Next, sensitivity was compared between each hydrogen sensor formed by using the hydrogen reaction catalytic layers 4 including platinum films having different thicknesses as illustrated in FIGS. 6A to 6C.

The sensitivity was measured using a gas chamber. The hydrogen concentration was adjusted by controlling a mixing ratio between a pure hydrogen gas and standard dry air using a mass flow controller. The pressure inside the chamber was maintained at approximately 0.1 MPa at the room temperature. In addition, a flow rate condition of 1 L/min was set for a chamber of 300 mL. A result of the experiment for the sensitivity is shown in Table 2.

TABLE 2

| Sample | Catalyst thickness [nm] | Frequency change/1% $H_2$ |
|---|---|---|
| A | 116 | 563 ppm |
| B | 386 | 488 ppm |
| C | 518 | 489 ppm |

Sample A of Table 2 is a sample in which the platinum film has a thickness of 116 nm. Sample B is a sample in which the platinum film has a thickness of 386 nm. Sample C is a sample in which the platinum film has a thickness of 518 nm.

In the experiment, sensitivity was measured three times for each sample, and an average value was obtained. As shown in Table 2, it was recognized that Sample A having the smallest film thickness had the highest sensitivity. Meanwhile, it was recognized that a difference of the sensitivity between Samples B and C was smaller relative to the difference of the film thickness.

Figure 14:
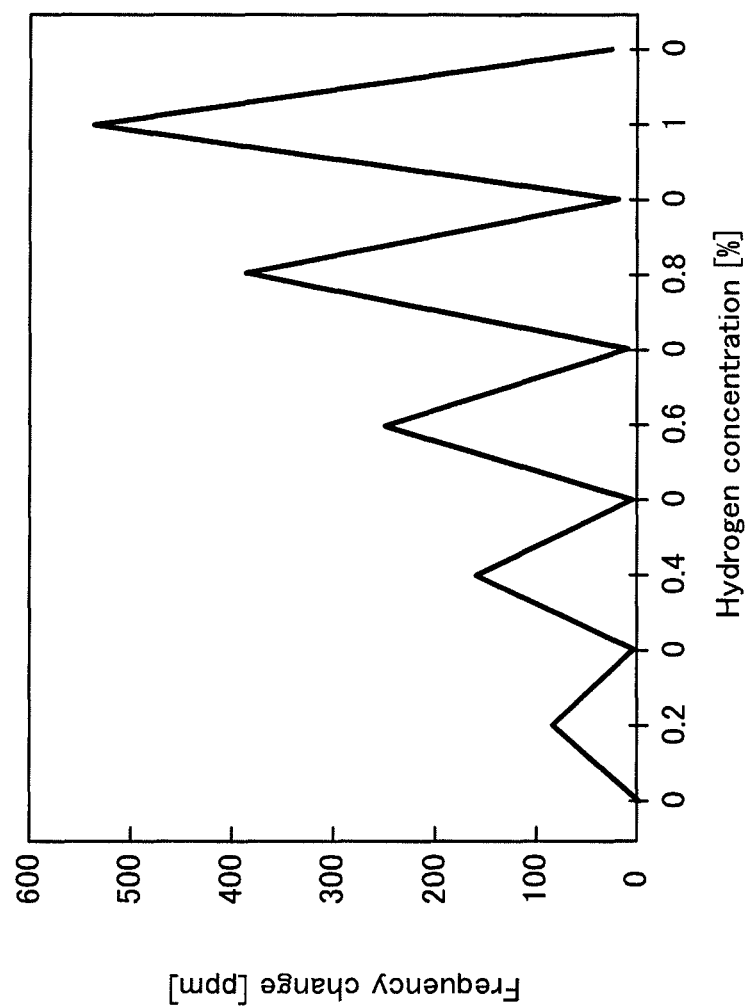
FIG. 14 is a graph illustrating a characteristic of the hydrogen sensor according to the invention.

FIG. 14 illustrates an output signal of the hydrogen sensor of this example for a hydrogen concentration range of 0 to 1%. It was recognized that linearity of sensitivity and a recovery characteristic are all excellent.

In recent years, interest in hydrogen energy such as a domestic fuel cell, a fuel cell vehicle (FCV), and a hydrogen station is increasing. For this reason, it is considered that demands for measurement of the hydrogen concentration will more and more increase in facilities or the like for producing, delivering, storing, and using hydrogen.

Using the hydrogen sensor according to the present invention, it is possible to easily detect a hydrogen concentration even when hydrogen is mixed in the air at a low concentration. In addition, it is possible to accurately measure the hydrogen concentration and provide remarkably high sensitivity even when the environmental temperature changes. Therefore, the hydrogen sensor according to the present invention is useful in measurement of the hydrogen concentration in each aspect described above.

This application is based on and claims priority to Japanese Patent Application No. 2015-183106, filed on Sep. 16, 2015, the entire content of which is incorporated herein by reference.

The invention claimed is:

1. A hydrogen sensor comprising:
   at least a first quartz vibrator and a second quartz vibrator formed in a quartz plate;
   a hydrogen reaction catalytic layer including a platinum film of platinum black formed on both sides of the first quartz vibrator; and
   a hydrogen non-reactive layer formed in the second quartz vibrator,
   wherein an average film thickness of the platinum film is in a range of greater than or equal to 70 nm and less than or equal to 150 nm, and
   wherein a hydrogen concentration is measured by measuring a temperature of the first quartz vibrator increased by heat of combustion caused by oxidization of hydrogen by the hydrogen reaction catalytic layer as a change of a natural frequency of the first quartz vibrator with respect to a natural frequency of the second quartz vibrator.

2. The hydrogen sensor according to claim 1, wherein the hydrogen reaction catalytic layer is formed by plating the platinum film.

3. The hydrogen sensor according to claim 1, wherein the hydrogen reaction catalytic layer is formed by coating platinum black powder.

4. A hydrogen sensor comprising:
   at least a first quartz vibrator and a second quartz vibrator formed in a quartz plate;
   a hydrogen reaction catalytic layer that is formed on both sides of the first quartz vibrator and includes a platinum film having a plurality of protrusions on its surface, the protrusions having a particulate shape in surface observation or having a dendritic shape, a needle-like shape, or a columnar shape in cross-sectional observation; and
   a hydrogen non-reactive layer formed in the second quartz vibrator,
   wherein an average film thickness of the platinum film is in a range of greater than or equal to 70 nm and less than or equal to 150 nm, and
   wherein a hydrogen concentration is measured by measuring a temperature of the first quartz vibrator increased by heat of combustion caused by oxidization of hydrogen in the hydrogen reaction catalytic layer as a change of a natural frequency of the first quartz vibrator with respect to a natural frequency of the second quartz vibrator.

* * * * *